United States Patent
Edvardsson et al.

(10) Patent No.: US 6,225,287 B1
(45) Date of Patent: May 1, 2001

(54) CRYSTALLINE FORMS

(75) Inventors: Daniel Edvardsson, Södertälje; Lena Hedström, Täby; Anita Lundblad, Västra Frölunda; Ursula Pettersson, Södertälje, all of (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/424,770

(22) PCT Filed: Sep. 2, 1999

(86) PCT No.: PCT/SE99/01514

§ 371 Date: Nov. 30, 1999

§ 102(e) Date: Nov. 30, 1999

(87) PCT Pub. No.: WO00/14110

PCT Pub. Date: Mar. 16, 2000

(30) Foreign Application Priority Data

Sep. 3, 1998 (SE) .................................................... 9802974

(51) Int. Cl.[7] ................. A61P 7/02; C07K 5/06; C07K 14/81; C07K 38/55

(52) U.S. Cl. ................................................. 514/19; 548/953

(58) Field of Search ................................. 514/19; 548/953

(56) References Cited

U.S. PATENT DOCUMENTS

| 4,315,011 | * | 2/1982 | Szantay et al. | 546/70 |
|---|---|---|---|---|
| 4,382,958 | * | 5/1983 | Duckworth | 564/363 |
| 5,830,865 | * | 11/1998 | Stjernfelt et al. | 514/18 |
| 5,939,392 | * | 8/1999 | Antonsson et al. | 514/18 |

FOREIGN PATENT DOCUMENTS

97/23499 A1   7/1997  (WO).

* cited by examiner

Primary Examiner—Jeffrey E. Russel
(74) Attorney, Agent, or Firm—Nixon & Vanderhye (57) ABSTRACT

There is provided $EtO_2C$—$CH_2$—(R)Cgl—Aze—Pab—OH, or a pharmaceutically-acceptable salt thereof, in a form which is substantially crystalline. It has been found that crystalline forms of $EtO_2C$—$CH_2$—(R)Cgl—Aze—Pab—OH have a high chemical and solid state stability when compared to amorphous forms of the compound.

46 Claims, 5 Drawing Sheets

CRYSTALLINE FORMS

FIELD OF THE INVENTION

This invention relates to new solid state forms of a drug, to pharmaceutical compositions containing them, and to processes for obtaining them.

BACKGROUND OF THE INVENTION

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active compound.

Further, in the manufacture of oral drug compositions, it is important that a reliable, reproducible and constant plasma concentration profile of drug is provided following administration to a patient. This is of particular importance in the manufacture of compositions comprising antithrombotic agents.

Chemical stability, solid state stability, and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically-pure as possible.

Amorphous materials may present significant problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, it is important, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound, either as such or in the form of a salt, will be. This can only be determined empirically.

PRIOR ART

International patent application WO 97/23499 discloses a number of compounds, which have been found to be useful as prodrugs of thrombin inhibitors, which thrombin inhibitors are of the general formula:

wherein $R^a$ represents H, benzyl or $C_{1-6}$ alkyl, Cgl represents cyclohexylglycine, Aze represents S-azetidine-2-carboxylic acid and Pab—H represents 4-aminomethyl-amidinobenzene. The active thrombin inhibitors are themselves disclosed in the earlier international patent application WO 94/29336.

WO 97/23499 also contains a specific disclosure of the compound:

wherein Pab—OH represents 4-aminomethyl-benzeneamidoxime. A process for the synthesis of this compound is described in Example 17 of WO 97/23499, where it is purified by preparative RPLC and isolated in an amorphous form.

Whether it is possible to provide $EtO_2C$—$CH_2$—(R)Cgl—Aze—Pab—OH in a crystalline form is not disclosed in WO 97/23499. Furthermore, no information is provided in relation to how this compound may be obtained in such a form.

DISCLOSURE OF THE INVENTION

Surprisingly, we have found that $EtO_2C$—$CH_2$—(R)Cgl—Aze—Pab—OH may be obtained in one or more forms that are substantially crystalline in nature.

Thus, according to a first aspect of the invention there is provided $EtO_2C$—$CH_2$—(R)Cgl—Aze—Pab—OH, or a pharmaceutically-acceptable salt thereof, in a substantially crystalline form (hereinafter referred to as "the compounds of the invention").

Although we have found that it is possible to produce $EtO_2C$—$CH_2$—(R)Cgl—Aze—Pab—OH, and salts thereof, in forms which are greater than 80% crystalline, by "substantially crystalline" we include greater than 10% (e.g. greater that 20%), preferably greater than 30%, and more preferably greater than 40% crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

Suitable pharmaceutically-acceptable salts which may be mentioned include inorganic, and organic, acidic and basic addition salts, such as hydrogen halide salts (e.g. HBr salts), carboxylic acid salts, lower alkanesulphonate salts (e.g. linear or branched $C_{1-6}$ alkanesulphonate, preferably $C_{1-3}$ alkanesulphonate, and especially ethane- and methane-sulphonate salts) and ammonium and amine salts. Toluene-sulphonate salts may also be mentioned. For a full list of salts that may be mentioned see Berge et al, J. Pharm. Sci., 66, 1 (1977). However, we prefer that the compounds of the invention are not in the form of a salt.

The compounds of the invention may be in the form of a solvate (by which we include a hydrate) or otherwise.

We have found, surprisingly, that the compounds of the invention have an improved stability when compared with $EtO_2C$—$CH_2$—(R)Cgl—Aze—Pab—OH prepared as described in WO 97/23499.

According to a further aspect of the invention, there is thus provided a stable form of $EtO_2C$—$CH_2$—(R)Cgl—Aze—Pab—OH, or a pharmaceutically-acceptable salt thereof.

The term "stability" as defined herein includes chemical stability and solid state stability.

By "chemical stability", we include that the compound, or salt, can be stored in an isolated form, or in the form of a formulation in which it is provided in admixture with pharmaceutically acceptable carriers, diluents or adjuvants (e.g. in an oral dosage form, such as tablet, capsule etc.), under normal storage conditions, with an insignificant degree of chemical degradation or decomposition.

By "solid state stability", we include that the compound, or salt, can be stored in an isolated solid form, or in the form of a solid formulation in which it is provided in admixture with pharmaceutically acceptable carriers, diluents or adjuvants (e.g. in an oral dosage form, such as tablet, capsule etc.), under normal storage conditions, with an insignificant degree of solid state transformation (e.g. crystallisation, recrystallisation, solid state phase transition, hydration, dehydration, solvatisation or desolvatisation).

Examples of "normal storage conditions" include temperatures of between minus 80 and plus 50° C. (preferably between 0 and 40° C. and more preferably room temperatures, such as 15 to 30° C.), pressures of between 0.1 and 2 bars (preferably at atmospheric pressure), relative humidities of between 5 and 95% (preferably 10 to 75%), and/or exposure to 460 lux of UV/visible light, for prolonged periods (i.e. greater than or equal to six months). Under such conditions, compounds of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

The compounds of the invention may be obtained advantageously by crystallising $EtO_2C$—$CH_2$—(R)Cgl—Aze—Pab—OH, or a salt of $EtO_2C$—$CH_2$—(R)Cgl—Aze—Pab—OH.

According to a further aspect of the invention, there is provided a process for the production of a compound of the invention which comprises crystallising $EtO_2C$—$CH_2$—(R)Cgl—Aze—Pab—OH, or a pharmaceutically-acceptable salt thereof.

It is possible to crystallise $EtO_2C$—$CH_2$—(R)Cgl—Me—Pab—OH and pharmaceutically-acceptable salts thereof with or without the presence of a solvent system (e.g. crystallisation may be from a melt, under supercritical conditions, or achieved by sublimation). However, we prefer that the crystallisation is from an appropriate solvent system.

We have found that it is possible advantageously to crystallise $EtO_2C$—$CH_2$—(R)Cgl—Aze—Pab—OH and pharmaceutically-acceptable salts thereof via crystallisation following dissolution of the compound or salt in question, or, more advantageously, from solutions which have been extracted from reaction solutions in which the compound or salt in question has been formed, or, particularly advantageously, from reaction solutions within which the compound or salt in question has been formed.

The solvent system may be heterogeneous or homogeneous and may thus comprise one or more organic solvents, such as alkyl acetates (e.g. linear or branched $C_{1-6}$ alkyl acetates, such as ethyl acetate, iso-propyl acetate and butyl acetate), lower (e.g. linear or branched $C_{1-6}$) alkyl alcohols (e.g. ethanol, iso-propanol), aliphatic (e.g. $C_{6-12}$, such as $C_{7-12}$, aliphatic) hydrocarbons (e.g. iso-octane and n-heptane) and aromatic hydrocarbons (e.g. toluene), dialkyl ketones (e.g. acetone, methyl iso-butyl ketone), acetonitrile and dialkyl ethers (e.g. di-iso-propyl ether), and/or aqueous solvents, such as water. Mixtures of any of the above-mentioned solvents may be used.

Different crystalline forms may have different solubilities in different organic solvents at any given temperature. In this respect, above-mentioned solvents may be employed as "antisolvents" (i.e. a solvent in which compounds of the invention are poorly soluble), and may thus aid the crystallisation process.

When the crystallisation takes place from a reaction solvent in which $EtO_2C$—$CH_2$—(R)Cgl—Aze—Pab—OH, or salt thereof, has been formed, or from a solvent following an extraction, suitable solvents thus include alkyl acetates (such as ethyl acetate), toluene, methyl iso-butyl ketone, lower alkyl alcohols (such as ethanol) etc.

Crystallisation of compounds of the invention from an appropriate solvent system may be achieved by attaining supersaturation in a solvent system which comprises $EtO_2C$—$CH_2$—(R)Cgl—Aze—Pab—OH, or salt thereof, (e.g. by cooling, by solvent evaporation and/or via the addition of anti-solvent (i.e. a solvent in which the compounds of the invention are poorly soluble (e.g. iso-octane, n-heptane, di-iso-propyl ether, toluene, acetone))), or by decreasing the solubility of the substance by the addition of a salt (such as NaCl or triethylamine-HCl).

Crystallisation temperatures and crystallisation times depend upon the concentration of the compound in solution, and upon the solvent system which is used.

Crystallisation may also be initiated and/or effected with or without seeding with crystals of the appropriate crystalline compound of the invention, and/or by adjustment of pH.

Compounds of the invention may be prepared in the form of a solvate (by which we include in the form of a hydrate, such as a monohydrate) or otherwise (e.g. in the form of an anhydrate). (The term "anhydrate", when used in this context, also includes "ansolvates".)

To ensure that anhydrate is produced, the solvent from which the crystallisation occurs should preferably be dried, either before or during the crystallisation process, in order to reduce the water content below a critical level, which should preferably not be exceeded during the crystallisation. Solvent may be dried during the crystallisation process, for example by decreasing the water content of a mixture of the compound to be crystallised and an appropriate organic solvent/aqueous solvent system (e.g. by increasing the amount of organic solvent that is present and/or removal of water by formation of an azeotrope, with successive distillations). Nonetheless, we have found that, for certain compounds of the invention that are anhydrates, such solvent drying is not necessary to ensure formation.

To ensure that monohydrate is produced, water must be present in the solvent from which the crystallisation occurs. The water content should preferably be kept above the critical level mentioned above during the crystallisation.

The "critical level" of water depends upon factors such as temperature, concentration in solution of the compound to be crystallised, impurity profile, and the solvent system which is employed, but may be determined non-inventively.

Thus, according to a further aspect of the invention, there is provided a compound of the invention which is in the form of an anhydrate, and a compound of the invention which is in the form of a monohydrate.

Crystalline anhydrate may be prepared by crystallising $EtO_2C$—$CH_2$—(R)Cgl—Aze—Pab—OH from one or more organic solvents (such as ethyl acetate, butyl acetate, acetone, ethanol, iso-propanol, iso-octane, di-isopropyl ether), water or mixtures thereof, which may have been dried, and/or may be dried during the crystallisation process, such that the water content is below the above-mentioned critical level. Thus, anhydrate may be produced by crystallisation from a solvent system which is substantially free of water.

By "substantially free of water", we include that the water content in the solvent system is below that which will result in the formation of, at most, 10% monohydrate, for any particular solvent system and set of crystallisation conditions.

Conversely, crystalline monohydrate may be prepared by crystallising EtO$_2$C—CH$_2$—(R)Cgl—Aze—Pab—OH from a solvent system comprising water, or a combination of water and one or more organic solvents, including organic solvents that are capable of dissolving water (e.g. ethyl acetate, ethanol, iso-propanol).

Crystalline monohydrate may also be obtained by dissolving the substance in an aqueous solution (e.g. water or mixtures of water and an alcohol, such as ethanol or iso-propanol) with a low pH followed by the addition of a weak base until the pH exceeds (and is preferably just above) a value of about 5 to 6 (at room temperature).

Crystalline monohydrate may also be prepared via other crystalline forms (such as an anhydrous form). This is achieved if the critical water content referred to above is exceeded during the crystallisation. Similarly, a crystalline anhydrate may be prepared from crystalline monohydrate by ad lowering the water content to below the above-mentioned critical water content during the crystallisation process.

Whether anhydrate or monohydrate crystallises is related to the kinetics and equilibrium conditions of the respective forms at the specific conditions. Thus, as may be appreciated by the skilled person, the crystalline form that is obtained depends upon both the kinetics and the thermodynamics of the crystallisation process. Under certain thermodynamic conditions (solvent system, temperature, pressure and concentration of compound of the invention), one crystalline form may be more stable than another (or indeed any other). However, crystalline forms that have a relatively low thermodynamic stability may be kinetically favoured. Thus, in addition, kinetic factors, such as time, impurity profile, agitation, the presence or absence of seeds, etc. may also influence which forms appear. Thus, the procedures discussed herein may be adapted by the skilled person as appropriate in order to obtain different crystalline forms.

Crystalline monohydrate may also be formed by elutriation of other crystalline forms (e.g. an anhydrous form) in water or a mixture of water and one or several organic solvents (such as ethanol or iso-propanol). The slurry which is formed should preferably be seeded with crystals of the crystalline monohydrate in order to ensure that an appropriate transformation takes place. As before, there is a critical water content, which depends on the solvent system which is employed and the temperature.

Thus, we have found that compounds of the invention in one crystalline form may be interconverted via recrystallisation to other crystalline forms.

According to a further aspect of the invention, there is provided a process for the conversion of one crystalline form of a compound of the invention to another which comprises recrystallising a compound of the invention from an appropriate solvent system.

Compounds of the invention that are anhydrates contain no more than 3%, preferably 2%, more preferably 1% and more preferably 0.5% (w/w) water, whether such water is bound (crystal water or otherwise) or not. Hydrates contain no less than 0.5 mol of water per mol of EtO$_2$C—CH$_2$—(R)Cgl—Aze—Pab—OH.

Preferred compounds of the invention are those that are in the form of an anhydrate. According to a further aspect of the invention, there is provided a compound of the invention that contains no more than 3% (w/w), preferably no more than 2% (w/w), water, whether such water is bound (crystal water or otherwise) or not.

When the compound of the invention is to be produced in the form of an acidic or basic addition salt, an appropriate amount of the appropriate acid or base may be added to the crystallisation mixture before crystallisation is effected. Alternatively, after addition of the salt, all of the solvent(s) may be evaporated and the resultant crystalline and/or amorphous form of the salt may be re-dissolved in an appropriate solvent system, such as ethyl formate or an alkyl alcohol such as n-heptanol or n-octanol, followed by agitation of the resultant solution with a view to inducing crystallisation.

Preferred addition salts include acidic addition salts, such as hydrobromide and methanesulphonate salts.

The preparation, and characterisation, of inter alia anhydrate, and monohydrate, forms of compounds of the invention are described hereinafter. Different crystalline forms of the compounds of the invention (e.g. anhydrate and monohydrate) may be readily characterised using X-ray powder diffraction (XRPD) methods, for example as described hereinafter.

In order to ensure that crystalline forms as described herein are prepared in the absence of other crystalline forms described herein, crystallisations are preferably carried out by seeding with nuclei and/or seed crystals of the desired crystalline form in the complete absence of nuclei and/or seed crystals of other crystalline forms described herein. This applies particularly to each of the specific crystalline forms, the preparation of which is described hereinafter in the Examples.

Compounds of the invention may be isolated using techniques which are well known to those skilled in the art, for example decanting, filtering or centrifuging.

Compounds may be dried using standard techniques. It will be appreciated by the skilled person that drying temperature and drying time may affect the solid state properties of compounds (or salts) that are in the form of solvates, such as hydrates (e.g. dehydration may occur at elevated temperatures and/or reduced pressure). For example, following the formation of crystalline monohydrate, there is a critical humidity below which the drying should not be performed, as the crystal water may be lost and a solid state transformation may occur, i.e. the crystal water will be lost if the crystals are dried at high temperatures or at very low pressures for a longer period.

We have found that, by employing the crystallisation process as described herein, it is possible to produce compounds of the invention with a chemical purity which is above that of the EtO$_2$C—CH$_2$—(R)Cgl—Aze—Pab—OH, or salt, which is to be isolated in the first instance.

Further purification of compounds of the invention may be effected using techniques which are well known to those skilled in the art. For example impurities may be removed by way of recrystallisation from an appropriate solvent system (e.g. ethyl acetate, iso-propanol, iso-octane, ethanol, water or a combination of these solvents). Suitable temperatures and times for the recrystallisation depend upon the concentration of the compound, or salt, in solution, and upon the solvent system which is used.

When compounds of the invention are crystallised, or recrystallised, as described herein, the resultant compound, or salt, is in a form which has the improved chemical and solid state stability mentioned hereinbefore.

Pharmaceutical Preparations and Medical Uses

In accordance with the invention, the compounds of the invention may be administered orally, intravenously, subcutaneously, buccally, rectally, dermally, nasally, tracheally, bronchially, by any other parenteral route, or via inhalation, in the form of a pharmaceutical preparation comprising the compound of the invention in a pharmaceutically acceptable dosage form. However we prefer that the compound of the invention is a form which is suitable for oral administration.

Depending on the disorder, and the patient to be treated, as well as the route of administration, the compounds may be administered at varying doses (see below).

The compounds of the invention may be further processed before formulation into a suitable pharmaceutical formulation. For example, the crystalline form may be milled or ground into smaller particles.

According to a further aspect of the invention, there is provided a pharmaceutical formulation including a compound of the invention in admixture with a pharmaceutically acceptable adjuvant, diluent or carrier.

The amount of compound of the invention which is employed in such a formulation will depend on the condition, and patient, to be treated, as well as the compound (s) which is/are employed, but can be determined non-inventively.

The compounds of the invention are useful because they are metabolised in the body following administration to form compounds which possess pharmacological activity. They are therefore indicated as pharmaceuticals, and in particular as prodrugs of pharmacologically-active compounds.

In particular, the compounds of the invention, although inactive to thrombin per se, are metabolised in the body to form potent inhibitors of thrombin, for example as demonstrated in the tests described in WO 97/23499. The compounds of the invention are expected to be useful in the treatment of conditions where inhibition of thrombin is required or desirable, including those described in WO 97/23499, the disclosure in which document is hereby incorporated by reference.

Suitable doses of the compound of the invention in the therapeutic and/or prophylactic treatment of mammalian, especially human, patients are in the range 2 to 200 mg per day at peroral administration, and 1 to 100 mg per day at parenteral administration and/or 0.001 to 20 mg/kg, preferably 0.01 to 5 mg/kg, body weight per day at peroral administration and 0.0005 to 10 mg/kg, preferably 0.005 to 2.5 mg/kg, body weight at parenteral administration.

According to a further aspect of the invention there is provided a method of treatment of a condition where inhibition of thrombin is required or desired, which method includes administering a therapeutically effective amount of a compound of the invention to a patient in need of such treatment.

For the avoidance of doubt, by "treatment" we include the therapeutic treatment, as well as the prophylaxis, of a condition.

The compounds of the invention have the advantage that they are in a form which provides for improved ease of handling. Further, the compounds of the invention have the advantage that they may be produced in forms which have improved chemical and solid state stability (including lower hygroscopicity). Thus, the compounds may be stable when stored over prolonged periods.

Compounds of the invention may also have the advantage that they may be crystallised in good yields, in a higher purity, in less time, more conveniently, and at a lower cost, than forms of $EtO_2C$—$CH_2$—(R)Cgl—Aze—Pab—OH prepared previously.

BRIEF DESCRIPTION OF THE DRAWINGS

The invention is illustrated, but in no way limited, by the following examples, with reference to the enclosed figures in which.

GENERAL PROCEDURES

X-ray powder diffraction analysis (XRPD) was performed on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a Siemens D5000 diffractometer and/or a Philips X'Pert MPD.

Differential scanning calorimetry (DSC) was performed using a Mettler DSC820 instrument, according to standard methods, for example those described in Höhne, G. W. H. et al (1996), *Differential Scanning Calorimetry*, Springer, Berlin.

Thermogravimetric analysis (TGA) was performed using a Mettler Toledo TGA850 instrument.

Forms prepared in accordance with the Examples below showed "essentially" the same XRPD diffraction patterns and/or DSC and/or TGA thermograms as other Examples disclosed below, when it was clear from the relevant patterns/thermograms (allowing for experimental error) that the same crystalline form had been formed. Thus, DSC onset temperatures may vary in the range ±5° C. (e.g. ±2° C.), and XRPD distance values may vary in the range ±2 on the last decimal place.

Example 1

Crystallisation of EtO2C—$CH_2$—(R)Cgl—Aze—Pab—OH 200 mg of $EtO_2C$—$CH_2$—(R)Cgl—Aze—Pab—OH (amorphous; obtained by freeze drying product obtained according to the method described in Example 17 of International Patent Application WO 97/23499) was dissolved in a di-iso-propylether:iso-propanol mixture (14 mL; 1:1). A homogeneous solution was initially formed which was allowed to stand for 24 hours at room temperature. Filtration and drying (ambient temperature) gave 160 mg of crystalline product.

Figure 1:
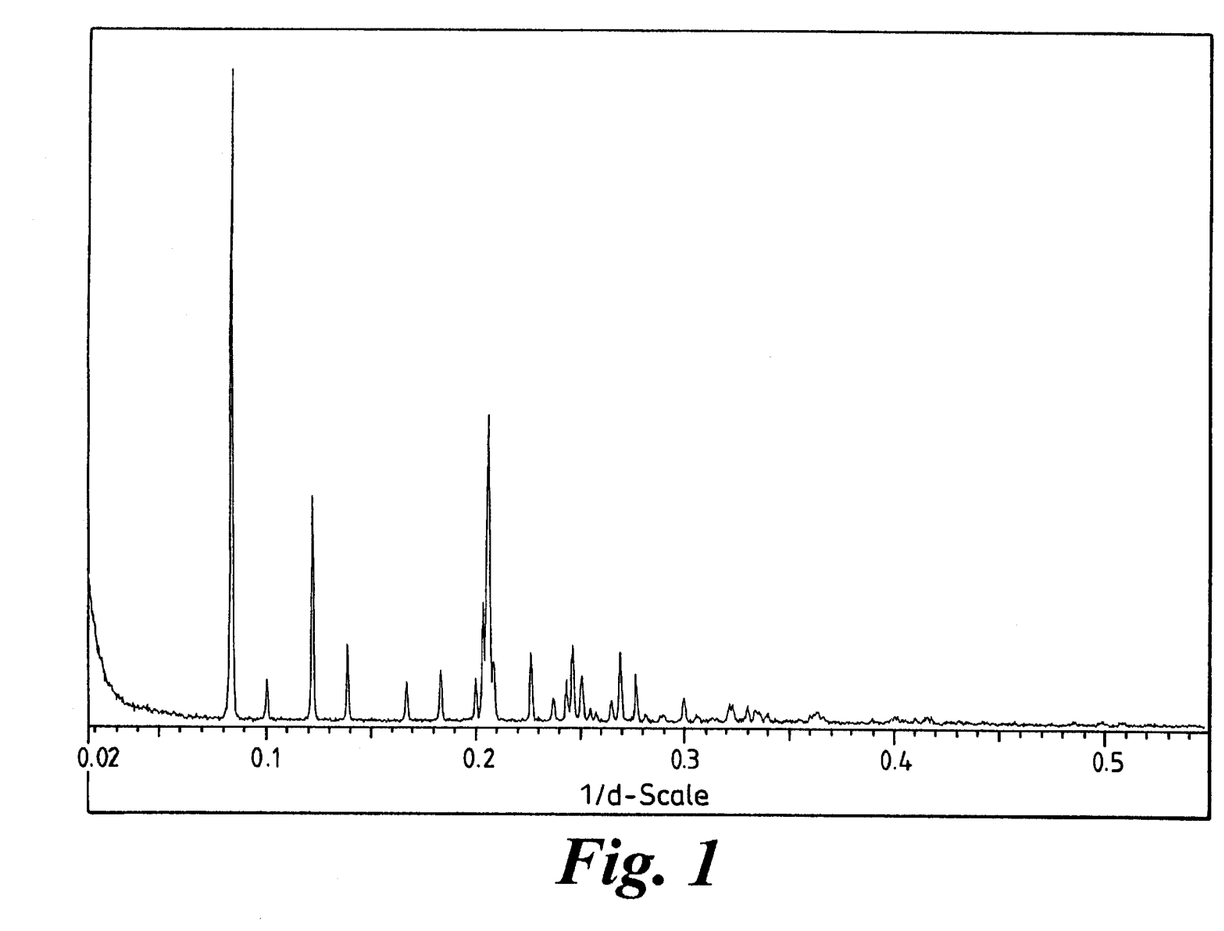
FIG. 1 shows a X-ray powder diffractogram for the crystalline form of $EtO_2C$—$CH_2$—(R)Cgl—Aze—Pab—OH obtained by way of Example 1.

The crystals were analyzed by XRPD and the results are tabulated below (Table 1, in which RI represents relative intensity) and are shown in FIG. 1.

TABLE 1

| d-value/Å | RI |
|---|---|
| 12.0 | vs |
| 10.0 | m |
| 8.2 | s |
| 7.2 | m |
| 6.0 | m |
| 5.5 | m |
| 5.0 | m |
| 4.92 | s |
| 4.85 | s |
| 4.80 | m |
| 4.42 | m |
| 4.22 | w |
| 4.11 | m |
| 4.06 | m |
| 3.99 | m |
| 3.78 | w |
| 3.72 | m |
| 3.62 | m |
| 3.34 | w |
| 3.11 | w |
| 3.10 | w |
| 3.03 | w |

A unit cell was determined from single crystal X-ray data. It was triclinic, with P1 symmetry, Z=1, and the following dimensions: a=5.149(1) Å, b=10.466(1) Å, c=12.317(1) Å, $\alpha$=80.32(1)°, $\beta$=79.78(1)°, $\gamma$=75.57(1)°,1 and V=627.2(2) Å$^3$.

DSC showed an endotherm with an extrapolated onset temperature of ca. 150° C. (ca. 113 J/g). TGA showed a decrease in mass of ca. 0.6% (w/w) around 150° C.

Example 2

Preparation of Crystalline EtO$_2$C—CH$_2$—(R)Cgl—Aze—Pab—OH from an Extracted Solution 70 mL of ethyl acetate was charged into a 140.3 g extracted solution of EtO$_2$C—CH$_2$—(R)Cgl—Aze—Pab—OH (prepared following an analogous synthesis to the procedure described in WO 97/23499, using ethanol as solvent, quenching with acetone, concentrating the resultant solution, and extracting with ethyl acetate). The solution thus prepared comprised ethyl acetate, ethanol and water (8.7% w/w). The solution was concentrated and dried by successive distillations, performed at 250 mbar and a bath temperature of 60° C. 70 mL of ethyl acetate was charged into the initial solution, which was concentrated until 46 g of solution remained. 103 mL of ethyl acetate was then charged into the solution, which was again concentrated until 70.5 g remained. Seeds of crystals obtained analogously to the method described in Example 3 were added and the resultant suspension was agitated for 3 hours at 40° C., cooled to 20° C. for 5 hours, then to 5° C. for 2.5 hours, and finally to –5° C. for 1 hour. The slurry was then agitated at the final temperature overnight and the crystals were filtered off, washed with ethyl acetate and dried at 40° C. under reduced pressure overnight.

The crystals were analyzed by XRPD, DSC and TGA, and showed essentially the same diffraction pattern, onset temperature, and decrease in mass, as those exhibited by the form obtained according to Example 1 above.

Recrystallisation of EtO$_2$C—CH$_2$—(R)Cgl—Aze—Pab—OH

Example 3

3.0 g EtO$_2$C—CH$_2$—(R)Cgl—Aze—Pab—OH (crude; obtained according to the method described in Example 2 above) was dissolved in 49.5 mL of isopropanol and 4.5 mL of purified water at 60° C. The solution was concentrated and dried by successive distillations, performed at 100 mbar and a bath temperature of 60° C. The solution was initially concentrated, until 17.5 g remained. 30 mL of iso-propanol was then charged into the resultant, and the solution was concentrated until 20 g remained. 1.8 g of iso-propanol and seeds of crystalline EtO$_2$C—CH$_2$—(R)Cgl—Aze—Pab—OH (obtained via a process that was analogous to the method described in Example 5 below) were then charged into the solution. The suspension was agitated for 3 hours at 40° C., and then cooled to 20° C. for 5 hours, to 5° C. for 2.5 hours, and to –5° C. for 1 hour. The slurry was then agitated at the final temperature overnight. The crystals were filtered off, washed with iso-propanol and dried at 40° C. under reduced pressure overnight.

The crystals were analyzed by XRPD, DSC and TGA, and showed essentially the same diffraction pattern, onset temperature, and decrease in mass, as those exhibited by the form obtained according to Example 1 above.

Example 4

4.0 g EtO$_2$C—CH$_2$—(R)Cgl—Aze—Pab—OH (crude; obtained according to the method described in Example 2 above) was dissolved in 2 mL of purified water, 16 mL of ethanol and 45 mL of ethyl acetate at 55° C. The solution was concentrated and dried by successive distillations performed at 250 mbar and a bath temperature of 55° C. The solution was initially concentrated, until 30 g remained. 32 mL of ethyl acetate was then charged into the resultant, and the solution was concentrated until 28 g remained. An additional 16 mL of ethyl acetate was added and the solution concentrated until 33 g remained. Seeds of crystalline EtO$_2$C—CH$_2$—(R)Cgl—Aze—Pab—OH (obtained via Example 3 above) was added to the solution. The suspension was agitated for 3 hours at 40° C., and then cooled to 20° C. for 5 hours, to 5° C. for 2.5 hours, and to –5° C. for 1 hour. The slurry was then agitated at the final temperature overnight. The crystals were filtered off, washed with ethyl acetate and dried at 40° C. under reduced pressure overnight.

The crystals were analyzed by XRPD, DSC and TGA, and showed essentially the same diffraction pattern, onset temperature, and decrease in mass, as those exhibited by the form obtained according to Example 1 above.

Example 5

3.0 g EtO$_2$C—CH$_2$—(R)Cgl—Aze—Pab—OH (crude; obtained according to the method described in Example 2 above) was dissolved in 4.5 mL of purified water and 49.5 mL of iso-propanol at 55 to 60° C. The solution was concentrated and dried by successive distillations performed at 100 mbar and a bath temperature of 60° C. The solution was initially concentrated until 16 g remained. The solution was agitated at 40° C., 18 mL of iso-octane was then charged into the resultant, and seeds of crystalline EtO$_2$C—CH$_2$—(R)Cgl—Aze—Pab—OH (obtained via Example 3 above) were added to the solution. The suspension was agitated for 3 hours at 40° C., and then cooled to 15° C. for 6 hours. The slurry was then agitated at the final temperature overnight. The crystals were filtered off, washed with a mixture of iso-propanol:iso-octane (1:1) and dried at 40° C. under reduced pressure overnight.

The crystals were analyzed by XRPD, DSC and TGA, and showed essentially the same diffraction pattern, onset temperature, and decrease in mass, as those exhibited by the form obtained according to Example 1 above.

Crystallisation of EtO$_2$C—CH$_2$—(R)Cgl—Aze—Pab—OH Monohydrate

Example 6

3.0 g of EtO$_2$C—CH$_2$—(R)Cgl—Aze—Pab—OH (crude; obtained according to the method described in Example 2 above) was dissolved in 1.5 mL of purified water, 10.5 mL of ethanol and 36 mL of ethyl acetate at 55° C. The solution was concentrated by distillation at 250 mbar and a bath temperature of 55° C. until 18 g remained. 30 mL of ethyl acetate was then charged into the solution, which was then concentrated until 21 g remained. 3.7 g of ethyl acetate, 0.9 g purified water and seeds of crystalline EtO$_2$C—CH$_2$—(R)Cgl—Aze—Pab—OH (obtained via Example 3 in above) were added to the solution. The suspension was agitated for 3 hours at 40° C., and then cooled to 20° C. for 5 hours, to 5° C. for 2.5 hours and to −5° C. for 1 hour. The slurry was then agitated at the final temperature for an additional day. The crystals were filtered off, washed with ethyl acetate and dried at 40° C. under reduced pressure (150 mbar) overnight.

Figure 2:
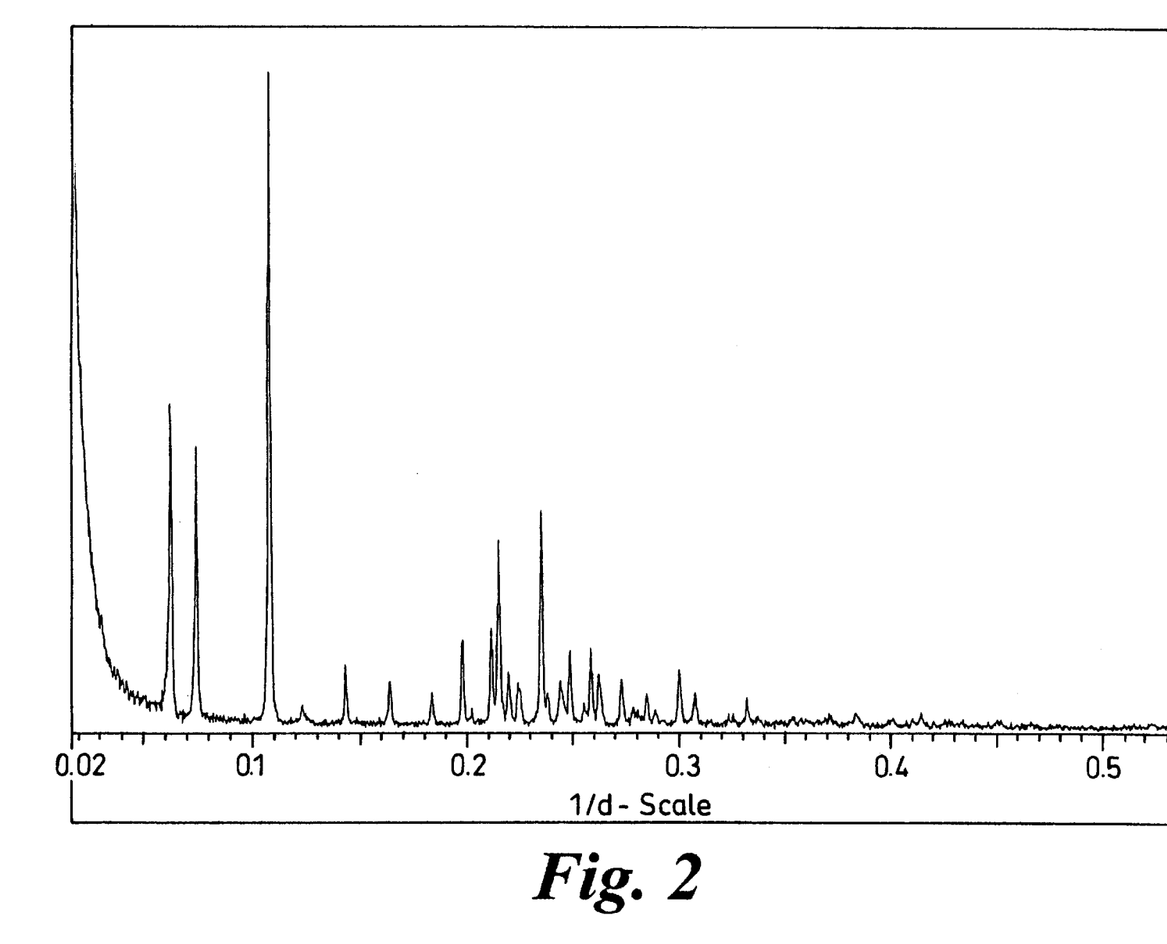
FIG. 2 shows a X-ray powder diffractogram for the crystalline form of $EtO_2C$—$CH_2$—(R)Cgl—Aze—Pab—OH monohydrate obtained by way of Example 6.

The crystals were analyzed by XRPD and the results are tabulated below (Table 2, in which RI represents relative intensity) and are shown in FIG. 2.

DSC showed an endotherm with an extrapolated onset temperature of ca. 94° C. (ca. 171 J/g). The crystals were analysed by Karl-Fischer titration and by TGA. TGA showed a decrease in mass of ca. 3.5% (w/w) around 85° C., corresponding to a monohydrate, and a decomposition starting around 210° C.

TABLE 2

| d-value/Å | RI |
| --- | --- |
| 16.4 | s |
| 13.7 | s |
| 9.4 | vs |
| 8.2 | w |
| 7.1 | m |
| 6.2 | m |
| 5.5 | w |
| 5.1 | m |
| 4.98 | w |
| 4.75 | s |
| 4.68 | s |
| 4.57 | m |
| 4.48 | m |
| 4.27 | s |
| 4.21 | w |
| 4.11 | m |
| 4.04 | m |
| 3.93 | w |
| 3.89 | m |
| 3.83 | m |
| 3.68 | m |
| 3.52 | w |
| 3.47 | w |
| 3.34 | m |
| 3.26 | w |
| 3.02 | w |
| 2.61 | w |
| 2.42 | w |

Example 7

5.0 g of EtO$_2$C—CH$_2$—(R)Cgl—Aze—Pab—OH (crude; obtained according to the method described in Example 2 above) was dissolved in 45 mL of isopropanol and 30 mL of purified water at 40° C. The solution was filtered until clear and concentrated by distillation under reduced pressure at 40° C. until 45 g remained. The solution was then cooled by 10° C./hour from 40 to −10° C. The slurry was then agitated for one day at the final temperature and the crystals filtered off, washed with iso-propanol and dried at 40° C. under reduced pressure (150 mbar) overnight.

The crystals were analyzed by XRPD, DSC and TGA, and showed essentially the same diffraction pattern, onset temperature, and decrease in mass, as those exhibited by the form obtained according to Example 6 above.

Example 8

2.7 g of EtO$_2$C—CH$_2$—(R)Cgl—Aze—Pab—OH (crude; obtained according to the method described in Example 2 above) was dissolved at 70° C. in 20 mL of ethanol and 30 mL of purified water. The solution was agitated and seeded with crystals of EtO$_2$C—CH$_2$—(R)Cgl—Aze—Pab—OH (obtained analogously to the method described in Example 6 above). The ethanol was slowly evaporated over two days. The crystals were filtered off and dried at 40° C. (200 mbar) over the weekend.

The crystals were analyzed by XRPD, DSC and TGA, and showed essentially the same diffraction pattern, onset temperature, and decrease in mass, as those exhibited by the form obtained according to Example 6 above.

Preparation of Crystalline EtO$_2$C—CH$_2$—(R)Cgl—Aze—Pab—OH.HBr

Example 9

7.08 g of EtO$_2$C—CH$_2$—(R)Cgl—Aze—Pab—OH (crude; obtained according to the method described in Example 2 above) was dissolved in 200 mL of iso-propanol and 2.52 g of 47% HBr at 40° C. The solution was evaporated to dryness at 40° C. and reduced pressure. An additional 120 mL of iso-propanol was charged into the resultant residue in order to rid it of its water content, and the resultant solution was evaporated to dryness. The amorphous substance was then dissolved in heptanol at ambient temperature. After some agitation, crystals formed. The slurry was agitated overnight, the crystals filtered off, washed with heptanol and dried at 80° C. under reduced pressure overnight.

The crystals were analyzed by titration with 0.1M NaOH and titration with 0.1M AgNO$_3$. The concentration of substance according to the titration with NaOH was 96.6% (w/w). The amount of Br according to the AgNO$_3$ titration was 13.9% (w/w) which is indicative, assuming a mono HBr salt, of a salt concentration of 96.4% (w/w). The remainder was solvent residue.

Figure 3:
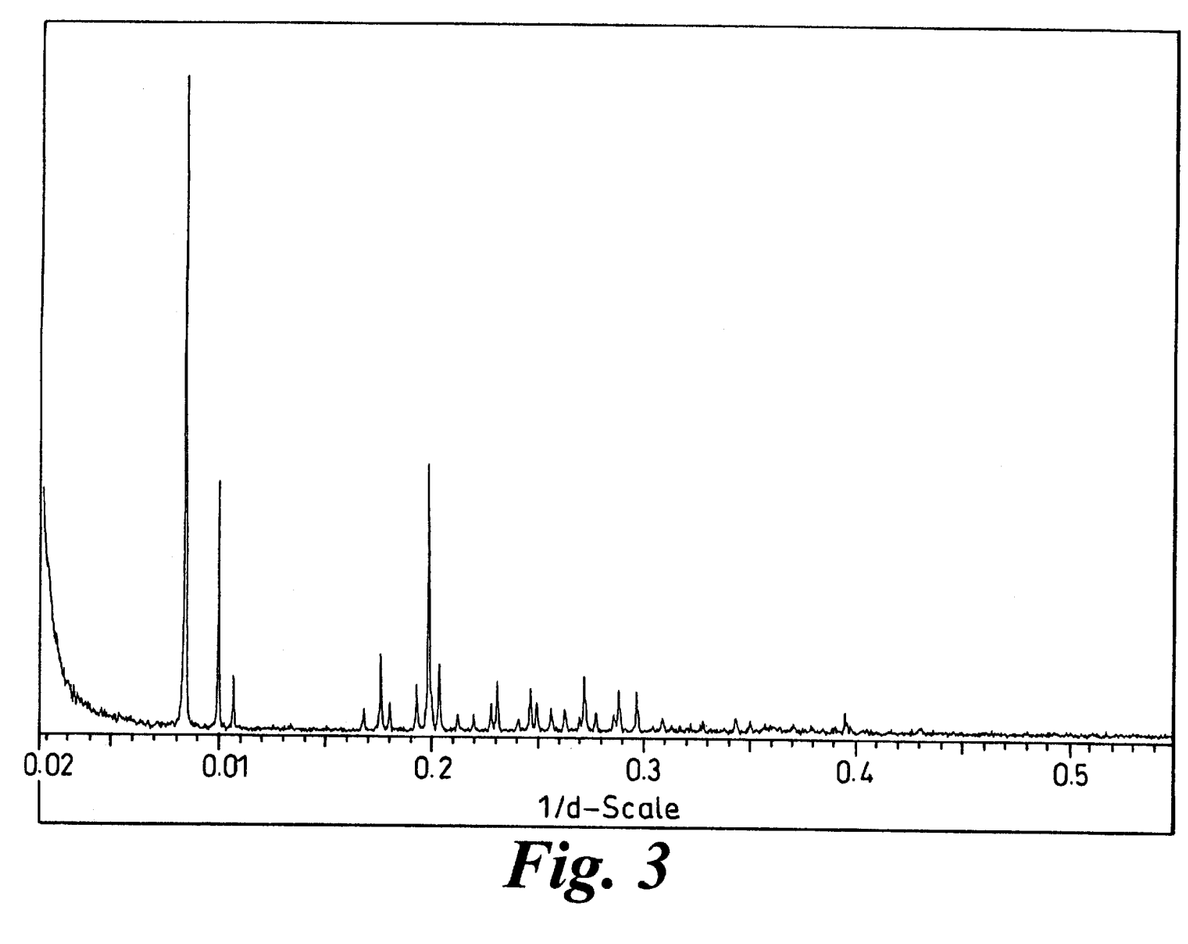
FIG. 3 shows a X-ray powder diffractogram for the crystalline form of $EtO_2C$—$CH_2$—(R)Cgl—Aze—Pab—OH hydrobromide obtained by way of Example 9.

The crystals were analyzed by XRPD and the results are tabulated below (Table 3, in which RI represents relative intensity) and are shown in FIG. 3.

TABLE 3

| d-value/Å | RI |
| --- | --- |
| 12.0 | vs |
| 10.1 | s |
| 9.5 | m |
| 6.0 | m |
| 5.7 | s |
| 5.6 | m |
| 5.2 | m |
| 5.1 | s |
| 4.95 | s |
| 4.74 | w |
| 4.57 | w |
| 4.41 | m |

TABLE 3-continued

| d-value/Å | RI |
|---|---|
| 4.35 | m |
| 4.17 | w |
| 4.07 | m |
| 4.03 | m |
| 3.92 | m |
| 3.82 | m |
| 3.72 | w |
| 3.69 | m |
| 3.62 | w |
| 3.51 | w |
| 3.48 | m |
| 3.38 | m |
| 3.25 | w |
| 3.06 | w |
| 2.92 | w |
| 2.86 | w |
| 2.71 | w |
| 2.53 | w |
| 2.33 | w |

DSC showed an endotherm with an extrapolated onset temperature of ca. is 166° C. (ca. 69 J/g).

Example 10

8 g of EtO$_2$C—CH$_2$—(R)Cgl—Aze—Pab—OH (crude; obtained according to the method described in Example 2 above) was dissolved in 120 mL of isopropanol and 2.9 g of 47% HBr at 40 to 50° C. The solution was evaporated to dryness, yielding an amorphous substance, which was dissolved in 1-octanol. The solution was agitated at ambient temperature and, after a while, crystallization occurred. The slurry was agitated overnight, the crystals filtered off, washed with 1-octanol and dried at 80° C. under reduced pressure over the weekend.

The crystals were analyzed by XRPD and DSC, and showed essentially the same diffraction pattern, and onset temperature, as those exhibited by the form obtained according to Example 9 above.

Example 11

1 g of EtO$_2$C—CH$_2$—(R)Cgl—Aze—Pab—OH (crude; obtained according to the method described in Example 2 above) was dissolved in 22 mL of iso-propanol and 0.36 g of 47% HBr at 45° C. The solution was filtered until clear and concentrated by distillation at reduced pressure until 3.85 g remained. The solution was agitated at 40° C. and 6 mL of toluene was added slowly. The solution was seeded with crystals of the HBr salt (obtained analogously to the method described in Example 9 above). When the suspension became white, an additional 9 mL of toluene was added. The slurry was agitated and the temperature was decreased to 20° C. The slurry was agitated overnight, the crystals filtered off, washed with toluene and dried at 40° C. under reduced pressure.

The crystals were analyzed by XRPD and DSC, and showed essentially the same diffraction pattern, and onset temperature, as those exhibited by the form obtained according to Example 9 above.

Preparation of Crystalline EtO$_2$C—CH=—(R)Cgl—Aze—Pab—OH.CH$_3$SO$_3$H

Example 12

10 g of EtO$_2$C—CH$_2$—(R)Cgl—Aze—Pab—OH (crude; obtained according to the method described in Example 2 above) was dissolved in 500 mL of isopropanol and 2.03 g of methanesulphonic acid (1 eq.) at 50° C. The solution was evaporated to dryness at 50° C. under reduced pressure resulting in the formation of an amorphous solid material. 1.5 g of this substance was dissolved in 15 mL ethyl formate, and the solution was agitated at ambient temperature overnight. The formed crystals were filtered off, washed with ethyl formate and dried at 40° C. under reduced pressure overnight. The crystals were analyzed by titration with 0.1 M NaOH, a two-phase titration. A concentration (99.9%) was calculated based on the assumption of formation of the mono-mesylate.

Figure 4:
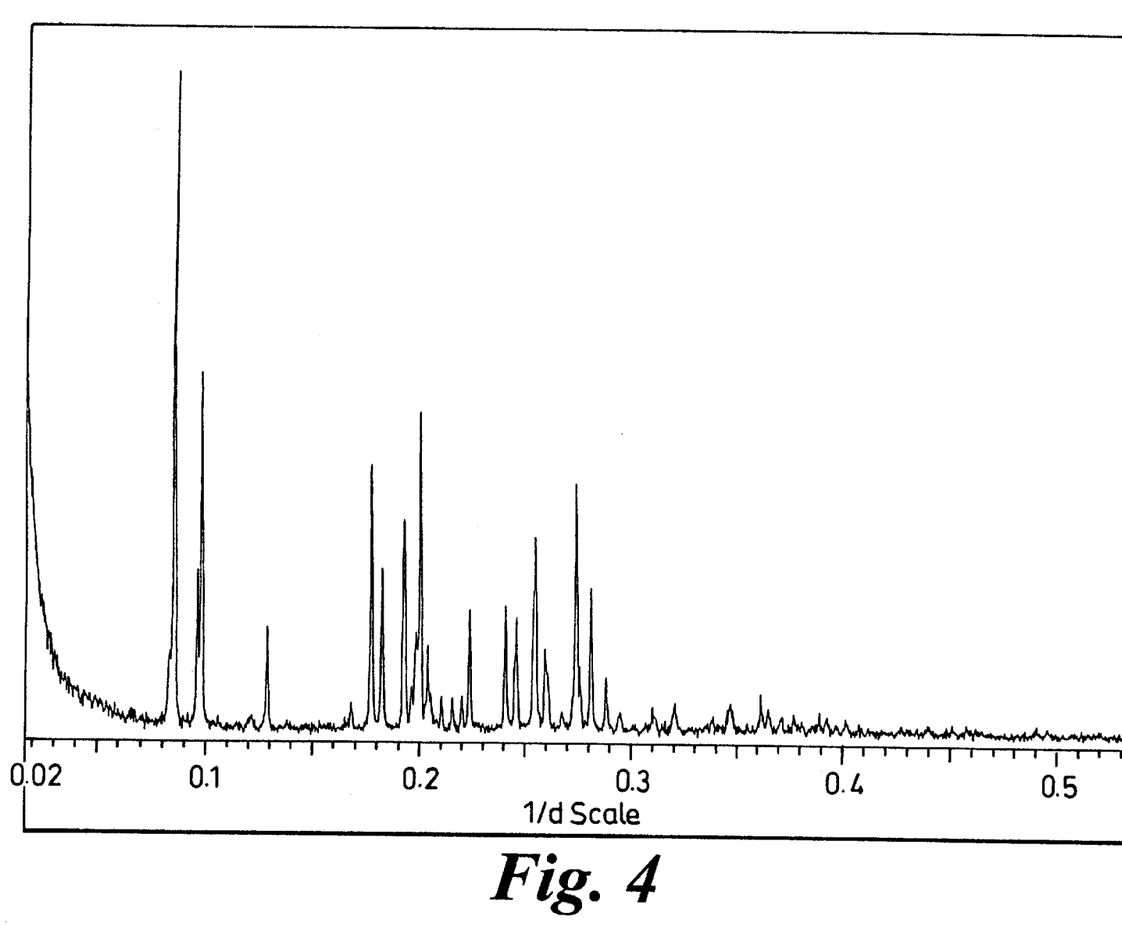
FIG. 4 shows a X-ray powder diffractogram for the crystalline form of $EtO_2C$—$CH_2$—(R)Cgl—Aze—Pab—OH methanesulphonate obtained by way of Example 12.

The crystals were analyzed by XRPD and the results are tabulated below (Table 4, in which RI represents relative intensity) and are shown in FIG. 4.

DSC showed an endotherm with an extrapolated onset temperature of ca. 134° C. (ca. 93 J/g).

TABLE 4

| d-value/Å | RI |
|---|---|
| 12.0 | s |
| 11.7 | vs |
| 10.4 | s |
| 10.2 | s |
| 8.3 | w |
| 7.8 | s |
| 6.0 | m |
| 5.6 | s |
| 5.5 | s |
| 5.2 | s |
| 5.1 | m |
| 5.0 | s |
| 4.98 | s |
| 4.90 | s |
| 4.75 | m |
| 4.63 | m |
| 4.54 | m |
| 4.46 | s |
| 4.15 | s |
| 4.06 | s |
| 3.92 | s |
| 3.84 | s |
| 3.74 | m |
| 3.65 | s |
| 3.56 | s |
| 3.47 | m |
| 3.39 | m |
| 3.22 | m |
| 3.12 | m |
| 2.95 | w |
| 2.88 | m |
| 2.76 | m |
| 2.74 | m |
| 2.69 | w |
| 2.65 | m |
| 2.54 | w |
| 2.52 | w |
| 2.49 | w |
| 2.27 | w |
| 2.21 | w |
| 2.04 | w |
| 2.02 | w |

Example 13

3.0 g of the amorphous substance from the first part of Example 12 above was dissolved in 15 mL octanol. The solution was agitated at ambient temperature overnight. The formed crystals were filtered off, washed with octanol and dried at 40° C. under reduced pressure overnight.

The crystals were analyzed by XRPD and DSC, and showed essentially the same diffraction pattern, and onset temperature, as those exhibited by the form obtained according to Example 12 above.

Preparation of Further Crystalline Form of
EtO$_2$C—CH$_2$—(R)Cgl—Aze—Pab—OH from
EtO$_2$C—CH$_2$—(R)Cgl—Aze—NH—CH$_2$—C$_6$H$_4$—
CN Example 14

0.0029 g of EDTA was dissolved in 16.4 g of aqueous hydroxylamine (50% (w/w)) and 110 mL ethanol, and was then charged into a jacketed glass reactor which was kept at a temperature of 32° C. 118.5 g of a solution of glycine, N-[1-cyclohexyl-2-[2-[[[[4-[cyano]phenyl]methyl]amino]carbonyl]-1-azetidinyl]-2-oxoethyl]-, ethyl ester, (S-(R*, S*)) (EtO$_2$C—CH$_2$—(R)Cgl—Aze—NH—CH$_2$—C$_6$H$_4$—CN) in butyl acetate (approx. concentration 36%(w/w)) was charged into the reactor. After 18 hours agitation, the solution/suspension was opaque. A sample was withdrawn to check the conversion using HPLC. The reaction was quenched by adding 14.4 mL acetone, followed by addition of 307 mL butyl acetate. The jacket temperature was set to 70° C. and the suspension was agitated for 1 hour at a temperature of 70° C. to dissolve the precipitate. The temperature of the thermostatic bath was then set to 40° C. and the solution was agitated for additional 78 hours. Particles were still present. The precipitate was filtered off. The filtrate was charged to a jacketed glass reactor and agitated at 40° C. An extraction program was started. All of the extractions were carried out at 40° C. 110 mL Na$_2$CO$_3$/NaCl (10%/10% (w/w)) was charged into the reactor, the solution was mixed for 10–20 minutes. Agitation was then stopped, allowing the phases to separate. The water phase was removed. 12.5 g ethanol and additional 110 mL of aqueous Na$_2$CO$_3$/NaCl (10%/10% (w/w)) was added, the solution was agitated for a few minutes and the phases were then allowed to separate. The water phase was removed, and 12.5 g ethanol and 110 mL of the aqueous Na$_2$CO$_3$/NaCl (10%/10% (w/w)) solution were added. The resultant solution was agitated for a few minutes and the two phases were then allowed to separate. The water phase was removed. 4 g of ethanol and 31 mL of water were added to the organic phase, which was agitated. The pH was adjusted to 7 by adding HCl (8% (w/w)). The solution was mixed, the two phases were allowed to separate and the water phase was removed. 52.9 g of the extraction solution, which comprised around 4 g of EtO$_2$C—CH$_2$—(R)Cgl—Aze—Pab—OH was charged into a round-bottom flask. 4 mL of a 35:65 (v/v) mixture of butyl acetate and ethanol was charged to the same flask. Solvent was evaporated using a rotary evaporator at a pressure of 100–200 mbar, and a bath temperature of 73° C. until 53.1 g solution remained. An additional 4 mL of the above solvent mixture was then added, and more solvent was evaporated until 54.74 g of solution remained. This procedure was repeated several times: 4 mL was added, the solution was concentrated by evaporation until 56.02 g remained, 4 mL was added, the solution was again concentrated until 56.04 g remained, an additional 4 mL was charged, and the solution was concentrated again until 33.43 g remained. 2.2 g of the solution was withdrawn for analysis of solvent composition by GC and water content by Karl Fischer titration. The water content was 1.0% (w/w). 0.34 mL of water was charged into the flask, which was placed in a thermostatic bath kept at 40° C. The solution was agitated using a teflon impeller for 3 hours and then cooled to 20° C. over 5 hours, to 5° C. over 2.5 hours and to −5° C. over one hour. The solution was then agitated for two hours at −5° C. The solution was still almost clear. The solution was then cooled to −20° C. over 1.5 hours and agitated at that temperature for additional 20 hours. A very viscous white slurry was formed. The crystals were filtered off by vacuum filtration and then dried overnight at 150 mbar and 40° C.

Figure 5:
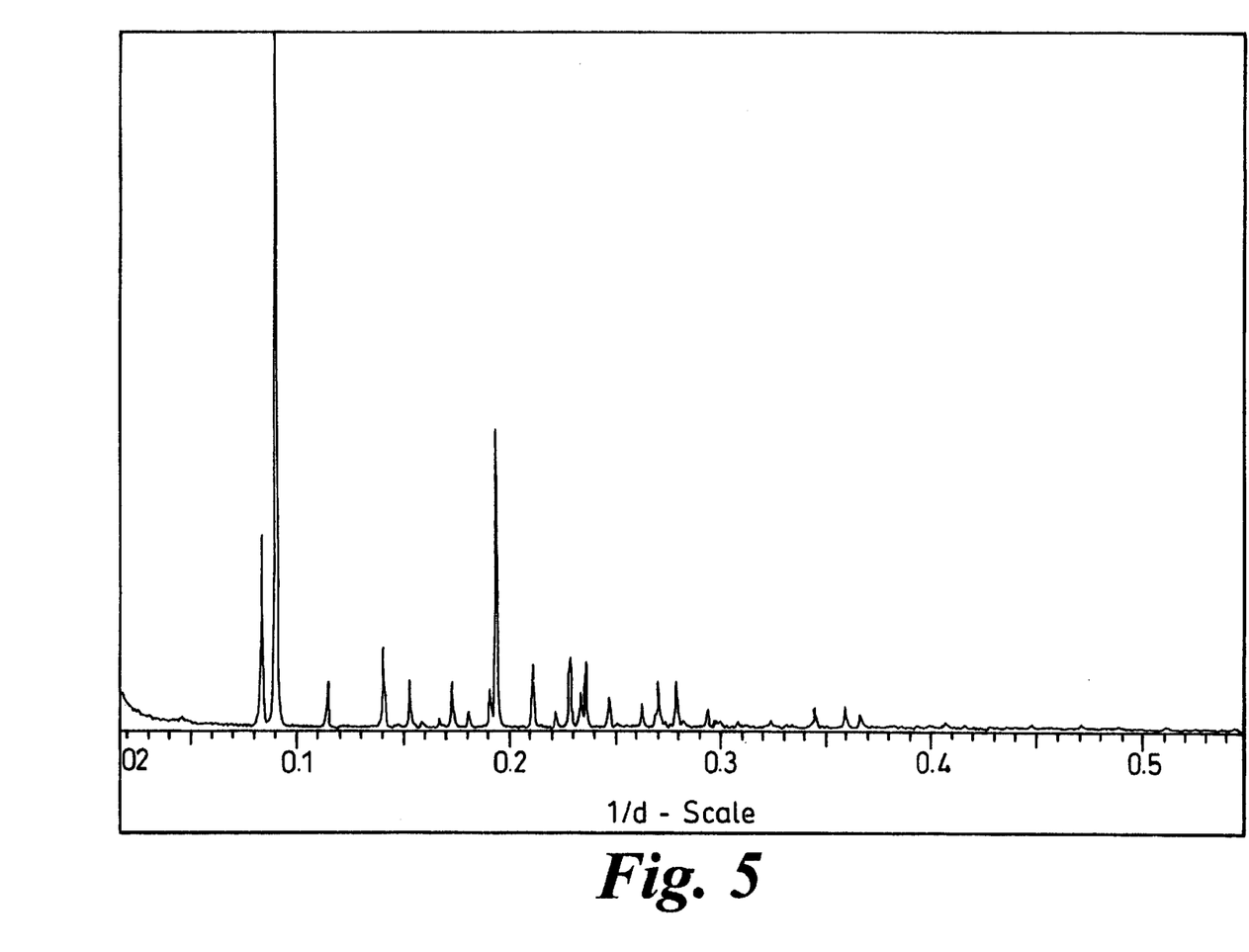
FIG. 5 shows a X-ray powder diffractogram for the crystalline form of $EtO_2C$—$CH_2$—(R)Cgl—Aze—Pab—OH obtained by way of Example 14.

The crystals were analysed by GC; XRPD, TGA, DSC and Karl Fischer titration. The XRPD results are tabulated below (Table 5, in which RI represents relative intensity) and are shown in FIG. 5.

TABLE 5

| d-value/Å | RI |
|---|---|
| 12.0 | s |
| 11.1 | vs |
| 8.8 | m |
| 7.2 | m |
| 6.8 | vw |
| 6.6 | m |
| 6.5 | vw |
| 6.4 | vw |
| 6.0 | w |
| 5.8 | m |
| 5.6 | w |
| 5.3 | m |
| 5.2 | s |
| 4.75 | m |
| 4.52 | w |
| 4.39 | m |
| 4.31 | w |
| 4.29 | m |
| 4.25 | m |
| 4.06 | w |
| 4.00 | vw |
| 3.82 | w |
| 3.73 | w |
| 3.71 | m |
| 3.69 | w |
| 3.66 | w |
| 3.59 | m |
| 3.55 | w |
| 3.41 | w |
| 3.37 | w |
| 3.34 | w |
| 3.29 | vw |
| 3.25 | w |
| 3.22 | vw |
| 3.10 | w |
| 3.03 | w |
| 3.00 | vw |
| 2.91 | w |
| 2.78 | w |
| 2.73 | w |
| 2.62 | vw |
| 2.51 | vw |
| 2.46 | w |
| 2.40 | w |
| 2.38 | w |
| 2.34 | vw |
| 2.29 | vw |
| 2.26 | vw |

DSC showed an endotherm with an extrapolated onset temperature of ca. 169° C. (ca. 142 J/g). TGA showed a decrease in mass of ca. 0.7% (w/w) around 170° C.

A unit cell was determined from single crystal X-ray data. It was orthorhombic, with P2$_1$2$_1$2$_1$ symmetry, Z=4, and the following dimensions: a=7.753(1) Å, b=14.331(1) Å, c=22.276(1) Å, α=β=γ=90°, and V=2471.6(4)Å$^3$.

Example 15

To a solution of around 9 g of EtO$_2$C—CH$_2$—(R)Cgl—Aze—NH—CH$_2$—C$_6$H$_4$—CN in a mixture of ethyl acetate/purified water (concentration of solute around 23% (w/v total), water concentration around 10% (w/w total)), 50 mL of ethanol was charged. The temperature of the solution was adjusted to 39° C. and a mixture of 0.61 mg EDTA and 3.62 g hydroxylamine (aq; 50% (w/w)) was charged into the reactor. After 1 h 50 min, seed crystals of EtO$_2$C—CH$_2$—(R)Cgl—Aze—Pab—OH anhydrate (prepared analogously to the method described in Example 14 above) were added. The suspension was agitated for 21 hours. 3.18 g of acetone was then charged into the reactor, and the suspension was agitated for an additional 30 minutes. The suspension was then heated to 60° C. over 3 hours. The temperature was kept at 60° C. for 6 hours and then cooled by decreasing the jacket temperature by 10° C./h until the temperature was close to −10° C. The crystals were then aged for an additional 2 hours. The crystals were separated from the mother liquor by filtration, washed with 20 mL, followed by a further 10 mL, of ethanol and then dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 16

To a solution of around 4.5 g of EtO$_2$C—CH$_2$—(R)Cgl—Aze—NH—CH$_2$—C$_6$H$_4$—CN in a mixture of ethyl acetate/purified water (concentration of solute around 24% (w/v total), water concentration around 10% (w/w total)), 9 mL of ethyl acetate and 11.2 mL of ethanol were charged. The temperature of the solution was adjusted to 41° C. and a mixture of 0.3 mg EDTA and 1.78 g of hydroxylamine (aq; 50% (w/w)) was charged into the round bottom flask. After 1 h 40 min, seed crystals of EtO$_2$C—CH$_2$—(R)Cgl—Aze—Pab—OH anhydrate (prepared analogously to the method described in Example 14 above) were added. The suspension was agitated for 22 hours. 2.79 g of acetone was then charged to the round bottom flask and the suspension was agitated for additional 19 hours. The crystals were separated from the mother liquor by filtration, washed with 2×10 mL of ethanol and then dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 17

To a solution of around 30 kg of EtO$_2$C—CH$_2$—(R)Cgl—Aze—NH—CH$_2$—C$_6$H$_4$—CN in 130 L of a mixture of ethyl acetate/water, 151 kg of ethanol was charged. The temperature of the solution was adjusted to 38° C. and a mixture of 2.1 g EDTA and 12.0 kg hydroxylamine (aq.; 51% (w/w)) was charged into the reactor. After around 1.5 to 2 hours, 171 g of seed crystals of EtO$_2$C—CH$_2$—(R)Cgl—Aze—Pab—OH anhydrate (prepared analogously to the method described in Example 14 above) were added. The suspension was agitated for around 23 hours. 19 kg of acetone was then charged into the reactor and the suspension was agitated for an additional 30 minutes. The suspension was then heated to 73° C. until all of the crystals were dissolved. The solution was cooled by decreasing the jacket temperature by 10° C./h. When the temperature was around 61° C., a further 172 g of the same seed crystals were added, and the cooling was continued until the temperature was close to −10° C. The crystals were then aged for an additional 11 hours. The crystals were separated from the mother liquor by centrifugation, washed with 90 kg iso-propanol and then dried at 40° C. under reduced pressure.

The crystals were analysed by XRPD, DSC and TGA. The analyses showed essentially the same XRPD pattern, DSC thermogram, and hi decrease in mass, as those exhibited by the form obtained according to Example 14 above.

Example 18

To a solution of around 5 g of EtO$_2$C—CH$_2$—(R)Cgl—Aze—NH—CH$_2$—C$_6$H$_4$—CN in an ethyl acetate/water mixture (concentration of solute around 26% (w/v total), water concentration around 10% (w/w total)), 12.5 mL of ethanol was charged. The temperature of the solution was adjusted to 41° C. and a mixture of 0.3 mg of EDTA and 7.49 g of hydroxylamine (aq; 50% (w/w)) were charged into the round bottom flask. After 1 h 40 min, seed crystals of EtO$_2$C—CH$_2$—(R)Cgl—Aze—Pab—OH anhydrate (prepared analogously to the method described in Example 14 above) were added. The suspension was agitated for 22 hours. 2.79 g of acetone was then charged into the round bottom flask and the suspension was agitated for an additional 19 hours. The crystals were separated from the mother liquor by filtration, washed with 2×10 mL of ethanol and then dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 19

To a solution of around 9 g of EtO$_2$C—CH$_2$—(R)Cgl—Aze—NH—CH$_2$—C$_6$H$_4$—CN in a mixture of ethyl acetate/purified water (concentration of solute around 23% (w/v total), water concentration around 10% (w/w total)), 56 mL of ethanol was charged. The temperature of the solution was adjusted to 50° C. and a mixture of 0.6 mg of EDTA and 3.49 g of hydroxylamine (aq; 50% (w/w)) was charged into the round bottom flask. After 1 h 40 min, 50 mg of seed crystals of EtO$_2$C—CH$_2$—(R)Cgl—Aze—Pab—OH anhydrate (prepared analogously to the method described in Example 14 above) were added. The suspension was agitated for 18 hours. 3.1 g of acetone was then charged to the round bottom flask and the suspension was agitated for additional 30 minutes. The suspension was then heated to 75° C. over 0.5 hours. 40 minutes later, the temperature of the bath was lowered to 25° C. (i.e. the crystal suspension was cooled by natural cooling). 21 hours later, the crystals were separated from the mother liquor by filtration and then dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Recrystallisation of EtO$_2$C—CH$_2$—(R)Cgl—Aze—Pab—OH Obtained Analogously to Methods of Examples 14 to 19

Example 20

2.0 g of crude EtO$_2$C—CH$_2$—(R)Cgl—Aze—Pab—OH (obtained analogously to methods described in Examples 14 to 19 above) was dissolved in a mixture of 13 mL of iso-propanol, 5 mL purified water and 0.65 g of ethanol at 70° C. The solution was agitated and cooled from 70 to 55° C. over 1.5 h. 2 mL of acetone was then added and the cooling was continued from 55° C. to 30° C. over 5 h, and from 30° C. to 0° C. over 3 h. The suspension was then agitated for 340 min at the final temperature. The crystals were filtered off and washed with 4 mL of iso-propanol and thereafter dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 21

2.0 g of crude EtO₂C—CH₂—(R)Cgl—Aze—Pab—OH (obtained analogously to methods described in Examples 14 to 19 above) was dissolved in a mixture of 1.5 mL of iso-propanol, 4.8 mL of purified water and 0.001 g of sodium hydroxide dissolved in 0.2 mL of purified water at 70° C. The solution was agitated for 1.5 h at 70° C. and thereafter cooled to 0° C. over 7 h. The suspension was agitated for 55 min at the final temperature. The crystals were filtered off and washed with 5 mL of iso-propanol and thereafter dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 22

1.5 g of crude EtO₂C—CH₂—(R)Cgl—Aze—Pab—OH (obtained analogously to methods described in Examples 14 to 19 above) was dissolved in a mixture of 10.13 mL of iso-propanol, 3.75 mL of purified water, and 1.13 mL of ethyl acetate at 70° C. The solution was cooled to 55° C. and thereafter to 0° C. over 5.5 h. The suspension was agitated for 695 min. at the final temperature. The crystals were filtered off and washed with 3 mL of iso-propanol and thereafter dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 23

31.0 kg of crude EtO₂C—CH₂—(R)Cgl—Aze—Pab—OH (obtained analogously to methods described in Examples 14 to 19 above) was dissolved in a mixture of 158 kg of iso-propanol and 78 kg of purified water at 71° C. A further 24 kg of iso-propanol was added following clear filtration. The solution was thereafter cooled to 57° C. and crystallisation was started by adding 78 g of seed crystals (obtained analogously to the method described in Example 14 above). The suspension was agitated whilst being cooled by 10° C./h to 0° C. The suspension was then agitated for 11 h at the final temperature. After centrifugation of the slurry, the crystals were washed with 84 kg of iso-propanol and thereafter dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 24

3.0 g of crude EtO₂C—CH₂—(R)Cgl—Aze—Pab—OH (obtained analogously to methods described in Examples 14 to 19 above) was dissolved in a mixture of 22.5 mL of iso-propanol, 7.5 mL of purified water and 37.1 mg of hydrochloric acid (32%) at 70° C. The solution was agitated for 3 h at 70° C. and thereafter cooled to 55° C. over 0.5 h, whereupon crystallisation started without seeding. The suspension was then cooled to 0° C. over 5.5 h. The suspension was agitated for 740 min at the final temperature. The crystals were filtered off and washed with 7.5 mL of iso-propanol and thereafter dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Example 25

3.0 g of EtO₂C—CH₂—(R)Cgl—Aze—Pab—OH (obtained analogously to methods described in Examples 14 to 19 above) was dissolved in a mixture of 22.5 mL iso-propanol and 7.5 mL purified water at 70° C. The solution was agitated for 3 h at 70° C. and thereafter cooled to 55° C. over 0.5 h, whereupon crystallisation started without seeding. The suspension was then cooled to 0° C. over 5.5 h. The suspension was agitated for 760 min at the final temperature. The crystals were filtered off and washed with 7.5 mL of iso-propanol and thereafter dried at 40° C. under reduced pressure.

The crystals were analysed by XRPD, DSC and TGA. The analyses showed essentially the same XRPD pattern, DSC thermogram, and decrease in mass, as those exhibited by the form obtained according to Example 14 above.

Abbreviations vs=very strong
s=strong
m=medium
w=weak
vw=very weak

What is claimed is:

1. A substantially crystalline form of EtO₂C—CH₂—(R)Cgl—Aze—Pab—OH which is in the form of an anhydrate.

2. A substantially crystalline form of EtO₂C—CH₂—(R)Cgl—Aze—Pab—OH or a pharmaceutically acceptable salt thereof that contains no more than 2% (w/w) water.

3. A substantially crystalline form of EtO₂C—CH₂—(R)Cgl—Aze—Pab—OH in the form of an anhydrate, characterized by a differential scanning calorimetry curve, at a heating rate of 5° C./min in a closed cup with a pinhole under flowing nitrogen, exhibiting an endotherm with an extrapolated onset temperature of about 150° C., a peak temperature of about 151° C., and an associated heat of about 113 J/gram, followed by an exotherm in the region 190–280° C.; and/or a X-ray powder diffraction pattern characterized by peaks with d-values at 12.0, 10.0, 8.2, 7.2, 6.0, 5.5, 5.0, 4.92, 4.85, 4.80, 4.42, 4.22, 4.11, 4.06, 3.99, 3.78, 3.72, 3.62, 3.34, 3.11, 3.10 and 3.03 Å.

4. A substantially crystalline form of EtO₂C—CH₂—(R)Cgl—Aze—Pab—OH in the form of an anhydrate, characterized by a differential scanning calorimetry curve, at a heating rate of 5° C./min in a closed cup with a pinhole under flowing nitrogen, exhibiting an endotherm with an extrapolated onset temperature of about 169° C., a peak temperature of about 170° C., and an associated heat of about 142 J/gram, followed by an exotherm in the region 180–280° C.; and/or a X-ray powder diffraction pattern characterized by peaks with devalues at 12.0, 11.1, 8.8, 7.2, 6.8, 6.6, 6.5, 6.4, 6.0, 5.8, 5.6, 5.3, 5.2, 4.75, 4.52, 4.39, 4.31, 4.29, 4.25, 4.06, 4.00, 3.82, 3.73, 3.71, 3.69, 3.66, 3.59, 3.55, 3.41, 3.37, 3.34, 3.29, 3.25, 3.22, 3.10, 3.03, 3.00, 2.91, 2.78, 2.73, 2.62, 2.51, 2.46, 2.40, 2.38, 2.34, 2.29, 2.26 Å.

5. A substantially crystalline form of EtO₂C—CH₂—(R)Cgl—Aze—Pab—OH which is in the form of a monohydrate.

6. A substantially crystalline form of EtO₂C—CH₂—(R)Cgl—Aze—Pab—OH in the form of a monohydrate, characterized by a differential is scanning calorimetry curve, at a heating rate of 5° C./min in a closed cup with a pinhole under flowing nitrogen, exhibiting an endotherm with an extrapolated onset temperature of about 94° C., a peak temperature of about 109° C., and an associated heat of about 171 J/gram, followed by an exotherm in the region 170–290° C.; and/or a X-ray powder diffraction pattern characterized by peaks with devalues at 16.4, 13.7, 9.4, 8.2, 7.1, 6.2, 5.5, 5.1, 4.98, 4.75, 4.68, 4.57, 4.48, 4.27, 4.21, 4.11, 4.04, 3.93, 3.89, 3.83, 3.68, 3.52, 3.47, 3.34, 3.26, 3.02, 2.61 and 2.42 Å.

7. A substantially crystalline form of $EtO_2C$—$CH_2$—(R)Cgl—Aze—Pab—OH which is in the form of a methanesulphonate salt.

8. A substantially crystalline form of $EtO_2C$—CH—(R)Cgl—Aze—Pab—OH methanesulphonate salt characterized by a differential scanning calorimetry curve, at a heating rate of 5° C./min in a closed cup with a pinhole under flowing nitrogen, exhibiting an endotherm with an extrapolated onset temperature of about 134° C., a peak temperature of about 137° C., and an associated heat of about 93 J/gram, followed by an exotherm in the region 140–220° C.; and/or a X-ray powder diffraction pattern characterized by peaks with d-values at 12.0, 11.7, 10.4, 10.2, 8.3, 7.8, 6.0, 5.6, 5.5, 5.2, 5.1, 5.0, 4.98, 4.90, 4.75, 4.63, 4.54, 4.46, 4,15, 4.06, 3.92, 3.84, 3.74, 3.65, 3.56, 3.47, 3.39, 3.22, 3.12, 2.95, 2.88, 2.76, 2.74, 2.69, 2.65, 2.54, 2.52, 2.49, 2.27, 2.21, 2.04 and 2.02 Å.

9. A process for the production of a compound as claimed in claim 1, 2, 3, 4, 5, 6, 7 or 8 which comprises crystallizing $EtO_2C$—$CH_2$—(R)Cgl—Aze—Pab—OH, or a pharmaceutically acceptable salt thereof.

10. A process as claimed in claim 9, which comprises crystallizing $EtO_2C$—$CH_2$—(R)Cgl—Aze—Pab—OH, or the salt, from a solvent.

11. A process as claimed in claim 10, wherein the solvent is selected from the group consisting of acetates, lower alkyl alcohols, aliphatic and aromatic hydrocarbons, dialkyl ethers, dialkyl ketones, acetonitrile, aqueous solvents, and mixtures thereof.

12. A process as claimed in claim 11 wherein the solvent is selected from the group consisting of $C_{1-6}$ alkyl acetates, linear or branched $C_{1-6}$ alkyl alcohols, $C_{6-12}$ aliphatic hydrocarbons, $C_{6-10}$ aromatic hydrocarbons, di-$C_{1-6}$ alkyl ethers, di-$C_{1-6}$ alkyl ketones, acetonitrile, water, and mixtures thereof.

13. A process as claimed in claim 12 wherein the solvent is selected from the group consisting of ethyl acetate, butyl acetate, ethanol, iso-propanol, iso-octane, n-heptane, toluene, di-iso propyl ether, acetone, methyl isobutyl ketone, acetonitrile, water, and mixtures thereof.

14. A process for the production of a compound as claimed in claim 1, 2, 3 or 4, which comprises crystallizing $EtO_2C$—$CH_2$—(R)Cgl—Aze—Pab—OH from a solvent which is substantially free of water.

15. A process for the production of a compound as claimed in claim 1, 2 or 4, which comprises crystallizing $EtO_2C$—$CH_2$—(R)Cgl—Aze—Pab—OH from a solvent which contains water.

16. A process for the production of a compound as claimed in claim 5 or 6, which comprises crystallizing $EtO_2C$—$CH_2$—(R)Cgl—Ac—Pab—OH from a solvent which contains water.

17. A process for the conversion of one crystalline form of a compound as claimed in claim 1, 2, 3, 4, 5, 6, 7 or 8, to another compound as claimed in claim 1, 2, 3, 4, 5, 6, 7 or 8, which comprises recrystallizing a compound as claimed in claim 1, 2, 3, 4, 5, 6, 7 or 8, from an appropriate solvent system.

18. A compound obtainable by a process according to claim 9.

19. A compound obtainable by a process according to claim 10.

20. A compound obtainable by a process according to claim 11.

21. A compound obtainable by a process according to claim 12.

22. A compound obtainable by a process according to claim 13.

23. A compound obtainable by a process according to claim 14.

24. A compound obtainable by a process according to claim 15.

25. A compound obtainable by a process according to claim 16.

26. A compound obtainable by a process according to claim 17.

27. A pharmaceutical formulation including a compound as defined in claim 1, 2, 3, 4, 5, 6, 7 or 8, in admixture with a pharmaceutically acceptable adjuvant, diluent or carrier.

28. A method of treatment of a condition where inhibition of thrombin is required or desired which method comprises administering a therapeutically effective amount of a compound according to claim 1, 2, 3, 4, 5, 6, 7 or 8, to a patient in need of such treatment.

29. A pharmaceutical formulation including a compound as defined in claim 18, in admixture with a pharmaceutically acceptable adjuvant, diluent or carrier.

30. A pharmaceutical formulation including a compound as defined in claim 19, in admixture with a pharmaceutically acceptable adjuvant, diluent or carrier.

31. A pharmaceutical formulation including a compound as defined in claim 20, in admixture with a pharmaceutically acceptable adjuvant, diluent or carrier.

32. A pharmaceutical formulation including a compound as defined in claim 21, in admixture with a pharmaceutically acceptable adjuvant, diluent or carrier.

33. A pharmaceutical formulation including a compound as defined in claim 22, in admixture with a pharmaceutically acceptable adjuvant, diluent or carrier.

34. A pharmaceutical formulation including a compound as defined in claim 23, in admixture with a pharmaceutically acceptable adjuvant, diluent or carrier.

35. A pharmaceutical formulation including a compound as defined in claim 24, in admixture with a pharmaceutically acceptable adjuvant, diluent or carrier.

36. A pharmaceutical formulation including a compound as defined in claim 25, in admixture with a pharmaceutically acceptable adjuvant, diluent or carrier.

37. A pharmaceutical formulation including a compound as defined in claim 26, in admixture with a pharmaceutically acceptable adjuvant, diluent or carrier.

38. A method of treatment of a condition where inhibition of thrombin is required or desired which method comprises administering a therapeutically effective amount of a compound according to claim 18, to a patient in need of such treatment.

39. A method of treatment of a condition where inhibition of thrombin is required or desired which method comprises administering a therapeutically effective amount of a compound according to claim 19, to a patient in need of such treatment.

40. A method of treatment of a condition where inhibition of thrombin is required or desired which method comprises administering a therapeutically effective amount of a compound according to claim 26, to a patient in need of such treatment.

41. A method of treatment of a condition where inhibition of thrombin is required or desired which method comprises administering a therapeutically effective amount of a compound according to claim 21, to a patient in need of such treatment.

42. A method of treatment of a condition where inhibition of thrombin is required or desired which method comprises administering a therapeutically effective amount of a compound according to claim 22, to a patient in need of such treatment.

43. A method of treatment of a condition where inhibition of thrombin is required or desired which method comprises administering a therapeutically effective amount of a compound according to claim 23, to a patient in need of such treatment.

44. A method of treatment of a condition where inhibition of thrombin is required or desired which method comprises administering a therapeutically effective amount of a compound according to claim 24, to a patient in need of such treatment.

45. A method of treatment of a condition where inhibition of thrombin is required or desired which method comprises administering a therapeutically effective amount of a compound according to claim 25, to a patient in need of such treatment.

46. A method of treatment of a condition where inhibition of thrombin is required or desired which method comprises administering a therapeutically effective amount of a compound according to claim 26, to a patient in need of such treatment.

* * * * *

UNITED STATES PATENT AND TRADEMARK OFFICE
CERTIFICATE OF CORRECTION

PATENT NO. : 6,225,287 B1  
DATED : May 1, 2001  
INVENTOR(S) : Edvardsson et al.

It is certified that error appears in the above-identified patent and that said Letters Patent is hereby corrected as shown below:

Column 5,
Line 23, delete "ad".

Column 7,
Line 40, delete "compound" and replace with -- compounds --.

Column 8,
Line 56, delete "EtO2C" and replace with -- $EtO_2C$ --.

Column 13,
Line 61, delete "$EtO_2C$—CH=—(R)Cgl—" and replace by
-- $EtO_2C$—$CH_2$—(R)Cgl— --.

Column 20,
Line 58, delete "devalues" and replace by -- d-values --.

Column 21,
Line 1, delete "is".
Line 62, delete "$EtO_2C$—$CH_2$—(R)Cgl—Ac—Pab—OH" and replace with
-- $EtO_2C$—$CH_2$—(R)Cgl—Aze—Pab—OH --.

Column 23,
Line 2, delete "claim 26" and replace by -- claim 20 --.

Signed and Sealed this

Eighth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,225,287 B1
DATED : May 1, 2001
INVENTOR(S) : Edvardsson et al.

It is certified that error appears in the above-identified patent and that said Letters Patent is hereby corrected as shown below:

Column 21,
Line 8, delete "devalues" and replace by -- d-values --.
Line 26, delete "4,15" and replace by -- 4.15 --.

Signed and Sealed this

Twenty-third Day of March, 2004

JON W. DUDAS
*Acting Director of the United States Patent and Trademark Office*